United States Patent

Effland et al.

[11] 3,952,025
[45] Apr. 20, 1976

[54] SUBSTITUTED 2-PHENYL-4,6,7,8-TETRAHYDROFURO AND 1,4,5,6,7,8-HEXAHYDROPYRROLO[3,2-C]AZEPINES

[75] Inventors: Richard C. Effland, Somerville; Larry Davis, Flemington; Grover C. Helsley, Pottersville, all of N.J.

[73] Assignee: American Hoechst Corporation, Bridgewater, N.J.

[22] Filed: Aug. 26, 1974

[21] Appl. No.: 500,254

[52] U.S. Cl.............................. 260/347.3; 260/347.7; 424/274; 424/278
[51] Int. Cl.² .................................... C07D 307/00

[58] Field of Search............ 260/346.1, 347.3, 347.4, 260/347.7

[56] References Cited
UNITED STATES PATENTS
3,142,619  7/1964  Ferdinand et al................ 260/347.3

Primary Examiner—Frederick E. Waddell
Attorney, Agent, or Firm—Curtis, Morris & Safford

[57] ABSTRACT

Substituted 2-phenyl-4,6,7,8-tetrahydrofuro- and 1,4,-5,6,7,8-hexahydropyrrolo[3,2-c]azepines and physiologically tolerable acid addition salts thereof possessing analgesic and tranquilizing properties, and a process for their preparation are described.

4 Claims, 1 Drawing Figure

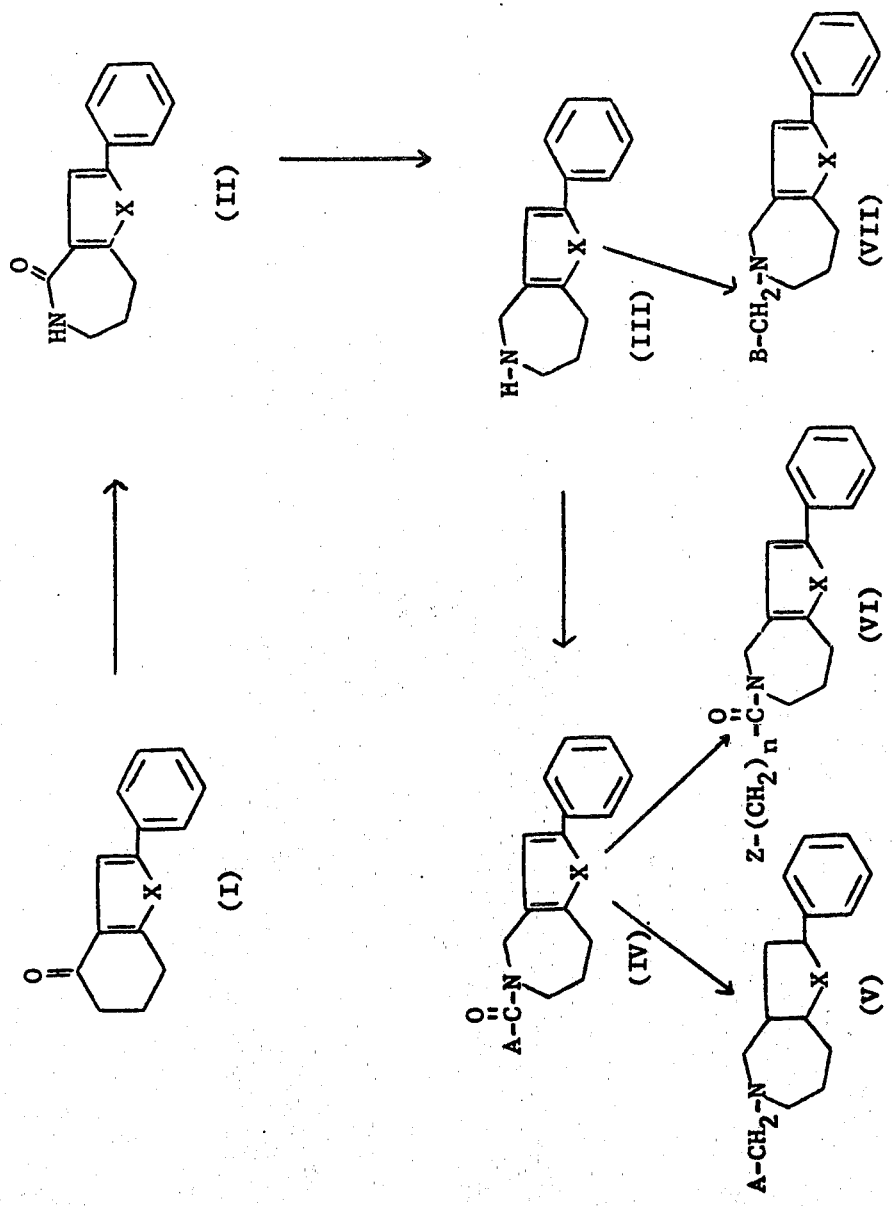

SUBSTITUTED 2-PHENYL-4,6,7,8-TETRAHYDROFURO AND 1,4,5,6,7,8-HEXAHYDROPYRROLO[3,2,-C]AZEPINES

This invention relates to substituted 2-phenyl-4,6,7,8-tetrahydrofuro- and 1,4,5,6,7,8-hexahydropyrrolo[3,2-c]azepines and physiologically tolerable acid addition salts thereof which possess analgesic and tranquilizing properties, and to a process for their preparation.

To the best of our knowledge, the compounds of the present invention have not heretofore been prepared or described. Substituted heterocyclic derivatives of azepines possessing antimicrobial activity are described in U.S. Pat. No. 3,758,501 (1973). However, the compounds of the present invention have significant structural differences and possess completely different activity.

The compounds of the invention have the formula:

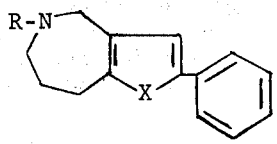

in which R is a linear or branched alkyl of from 1 to 4 carbon atoms, alkenyl of from 3 to 6 carbon atoms, cycloalkylalkyl of from 4 to 8 carbon atoms, alkanoyl of from 2 to 6 carbon atoms, haloalkanoyl of from 2 to 6 carbon atoms, alkoxycarbonyl of from 2 to 6 carbon atoms, cycloalkylcarbonyl of from 4 to 7 carbon atoms, benzoyl, alkoxybenzoyl of from 8 to 10 carbon atoms, halobenzoyl, benzoylalkyl of from 8 to 11 carbon atoms, halobenzoylalkyl of from 8 to 11 carbon atoms, phenalkyl of from 7 to 10 carbon atoms, alkoxyphenalkyl of from 8 to 11 carbon atoms, halophenylalkyl of from 7 to 16 carbon atoms, phenylpiperazinylacetyl or alkoxyphenylpiperazinylacetyl; X is O or $NR_1$; and $R_1$ is alkyl of from 1 to 6 carbon atoms, cycloalkyl of from 3 to 6 carbon atoms, cycloalkylalkyl of from 4 to 7 carbon atoms, or phenyl.

The compounds of the present invention can be prepared in a multi-step sequence of reactions as described below and illustrated in the attached drawing, in which X is as defined earlier, A is alkyl, cycloalkyl, phenyl, alkoxy, haloalkyl or, in Formula V, hydrogen, Z is an amino group and B is alkyl, benzoylalkyl, alkoxyalkyl or alkenyl.

A tetrahydroketone of Formula I is prepared in the manner described in Stetter and Steinhold; Chem. Ber., 88, 271-4(1955). The ketone is subjected to the conditions of the Schmidt rearrangement to provide an azepinone of Formula II. The azepinone is reduced to provide the azepine of Formula III. In a preferred method, lithium aluminum hydride is used as the reducing agent in refluxing tetrahydrofuran as the solvent for from 30 minutes to 24 hours. The azepino nitrogen can be substituted by several methods. Acylation is effected by reacting an azepine with a suitable acylating compound in an organic solvent in the presence or absence of an acid scavenger for from 30 minutes to 30 hours at a reaction temperature of from about 10° to 60°C. to give a compound of the invention of Formula IV. This acylated azepine can be reduced by methods known to the art to give an alkylated azepine of Formula V. When a compound of Formula IV is a halogenated alkanoylazepine, it can be reacted with an amine in the presence or absence of an acid scavenger for from 30 minutes to 30 hours at from about 15° to 75C. to yield a compound of the invention of Formula VI. Alternatively, a compound of Formula III can be alkylated in the presence of an organic solvent, and in the presence or absence of an acid scavenger and a catalyst for from 1 to 120 hours at a temperature from ambient to the boiling point of the solvent to yield a compound of the invention of Formula VII. In one preferred embodiment of the method, n-butanol is used as the solvent, potassium iodide crystals are used as the catalyst, and potassium carbonate is used as the acid scavenger. The introduction of a ketoalkyl subsituent is sometimes effected by reacting with a ketal of a haloketone. The ketal is used to reduce the rate of by-product formation and thereby to effect an increase in yield.

Compounds of the invention are useful as analgesic agents due to their ability to alleviate pain in mammals. The activity of the compounds is demonstrated in the 2-phenyl-1, 4-benzoquinone-induced writhing test in mice, a standard assay for analgesia [Proc. Soc. Expt'l. biol. Med., 95, 729 (1957)]. For example, an approximately 50% inhibition of phenylquinone writhing is effected by 2-phenyl-5-ethyl-4,6,7,8-tetrahydrofuro-[3,2-c]azepine hydrochloride, and 2-phenyl-5-methyl-4,6,7,8-tetrahydrofuro[3,2-c]azepine hydrochloride at doses of 31 and 12.5 mg./kg., respectively. Similarly, 50 mg./kg. doses of 2-phenyl-4,6,7,8-tetrahydro-5-(3,4,5-trimethoxybenzyl)furo-[3,2-c]azepine hydrochloride, 2-phenyl-5-acetyl-4,6,7,8-tetrahydrofuro[3,2-c]azepine and 1-cyclopropyl-2-phenyl-5-ethyl-1,4,5,6,7,8-hexahydropyrrolo[3,2-c]azepine oxalate exhibit a 48, 47 and 54% inhibitions of phenylquinone writhing, respectively. These data demonstrate that compounds of the invention are useful for the alleviation of pain in mammals when administered in doses ranging from 0.2 to about 50 mg./kg., of body weight per day.

Compounds of the invention are also useful as tranquilizers due to their depressant action on the central nervous system of mammals. This activity is demonstrated in the mouse observation procedure, a standard assay of central nervous depressants [Psychopharmacologia, 9, 259 (1966)]. Thus, for example, the minimum effective dose (MED) at which 1-cyclopropyl-2-phenyl-5-[3-(p-fluorobenzoyl)propyl]-1,4,5,6,7,8-hexahydropyrrolo[3,2-c]-azepine hydrochloride displays significant effects on behavior and reflex depression together with muscle relaxation is 25 mg./kg. Similarly, MED's of other compounds are:

|  | MED (mg./kg.) |
|---|---|
| 2-Phenyl-5-[3-(p-fluorobenzoyl)propyl]-4,6,7,8-tetrahydrofuro[3,2-c]azepine hydrochloride | 40 |
| 2-Phenyl-5-ethyl-4,6,7,8-tetrahydrofuro[3,2-c]-azepine hydrochloride | 50 |
| 1,2-Diphenyl-5-isopropyl-1,4,5,6,7,8-hexahydropyrrolo[3,2-c]azepine hydrochloride | 50 |

| -continued MED (mg./kg.) | |
|---|---|
| 1,2-Diphenyl-5-ethyl-1,4,5,6,7,8-hexahydropyrrolo-[3,2-c]azepine hydrochloride | 50 |
| 1-Cyclopropyl-2-phenyl-5-[3-(p-fluorobenzoyl)propyl]-1,4,5,6,7,8-hexahydropyrrolo[3,2-c]azepine hydrochloride | 25 |

These data demonstrate that compounds of the invention are useful for depressing the central nervous systems of mammals in doses ranging from 0.5 to about 50 mg./kg. of body weight per day. Examples of the compounds of the invention are:

2-Phenyl-5-benzoyl-4,6,7,8-tetrahydrofuro[3,2-c]azepine;
2-Phenyl-5-propionyl-4,6,7,8-tetrahydrofuro[3,2-c]azepine;
2-Phenyl-5-butyryl-4,6,7,8-tetrahydrofuro[3,2-c]azepine;
2-Phenyl-5-cyclohexylcarbonyl-4,6,7,8-tetrahydrofuro[3,2-c]azepine;
2-Phenyl-5-butoxycarbonyl-4,6,7,8-tetrahydrofuro[3,2-c]azepine;
2-Phenyl-5-cyclohexylmethyl-4,6,7,8-tetrahydrofuro[3,2-c]azepine;
2-Phenyl-5-(p-chlorobenzoyl)-4,6,7,8-tetrahydrofuro[3,2-c]azepine;
2-Phenyl-5-phenylbutyl-4,6,7,8-tetrahydrofuro[3,2-c]azepine;
1,2-Diphenyl-5-phenylpiperazinoacetyl-1,4,5,6,7,8-hexahydropyrrolo-[3,2-c]azepine;
1-Hexyl-2-phenyl-5-ethyl-1,4,5,6,7,8-hexahydropyrrolo[3,2-c]azepine;
1-Methyl-2-phenyl-5-cyclopropylethyl-1,4,5,6,7,8-hexahydropyrrolo-[3,2-c]azepine;
1-Cyclohexyl-2-phenyl-5-ethyl-1,4,5,6,7,8-hexahydropyrrolo[3,2-c]-azepine; and
1-Cyclopentylethyl-2-phenyl-5-propyl-1,4,5,6,7,8-hexahydropyrrolo[-[3,2-c]azepine.

The compounds of the present invention may be administered to a patient by any convenient route such as orally, intramuscularly, intravenously, subcutaneously, or intraperitoneally. The preferred route of administration is oral, for example, with an inert diluent or with an edible carrier or in gelatin capsules or tablets.

For the purpose of oral therapeutic administration, the active compounds of this invention may be incorporated with excipients and used in the form of tablets, troches, capsules, elixirs, suspensions, syrups, wafers, chewing gum, and the like. These preparations should contain at least 0.5% of active compound, but may be varied depending upon the particular form and may conveniently be between 7 to about 70% by weight of the unit. The amount of active compound in such compositions is such that a suitable dosage will be obtained. Preferred compositions and preparations according to the present invention are prepared so that an oral dosage unit form contains between 10 and 200 milligrams of active compound.

The tablets, pills, capsules, troches, and the like may also contain the following ingredients: a binder such as gum tragacanth or gelatin; an excipient such as starch or lactose, a disintegrating agent such as alginic acid, potato starch and the like; a lubricant such as magnesium stearate; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or both. A syrup may contain, in addition to the active compounds sucrose as a sweetening agent, and certain preservatives, dyes and colorings and flavors. Materials used in preparing these various compositions must be pharmaceutically pure and non-toxic in the amounts utilized.

Pharmaceutically acceptable acids useful for preparing the physiologically tolerable acid addition salts include inorganic acids such as hydrochloric, hydrobromic, sulfuric, nitric, phosphoric and perchloric acids, as well as organic acids such as oxalic, tartaric, citric, acetic, severinic, maleic and ethane disulfonic acids.

EXAMPLE 1 a. A solution of 5.0 g. of 3-(1-pyrrolodinyl)-2-cyclohexan-1-one in 30 ml. of anhydrous dimethylformamide is treated dropwise over twenty minutes under nitrogen with a solution of 6.0 g. of phenacyl bromide in 10 ml. of anhydrous dimethylformamide. The mixture is stirred for 47 hours at 80°C., allowed to cool to ambient temperature, and then poured into water and stirred for 30 minutes. The resulting suspension is extracted with chloroform, the chloroform extracts are combined, washed with water and dried. The solvent is removed and the residue is dried under high vacuum and crystallized from ethanol to yield 4-oxo-2-phenyl-4,5,6,7-tetrahydrobenzo[b]furan, m.p. 132°–134°C.

b. 2.6 g. of sodium azide are added portionwise over a period of 30 minutes to a solution of 6.0 g. of 4-oxo-2-phenyl-4,5,6,7-tetrahydrobenzo[b]furan in 100 g. of polyphosphoric acid. After stirring at 100°C. for 24 hours, the mixture is poured into water and the resulting brown precipitate is collected, washed with water and dried. This material is recrystallized from carbon tetrachloride to give 4-oxo-2-phenyl-4,6,7,8-tetrahydrofuro[-[3,2-c]azepine, m.p. 160°–164°C.

c. A suspension of 10.2 g. of 4-oxo-2-phenyl-4,6,7,8-tetrahydrofuro[3,2-c]azepine in 100 ml. of dry tetrahydrofuran is added dropwise to a refluxing mixture of 3.4 g. of lithium aluminum hydride in 200 ml. of dry tetrahydrofuran. The mixture is allowed to reflux for 20 hours, then cooled and quenched with water and a saturated solution of ammonium chloride. The mixture is filtered, the organic layer is collected, diluted with ether, washed with water, dried and concentrated to a brown oil, which solidifies to a tan solid. The solid is converted to the hydrochloride and recrystallized from an isopropanol-ether mixture to yield 2-phenyl-4,6,7,8-tetrahydrofuro[3,2-c]azepine hydrochloride, m.p. 267°C., dec.

Analysis: Calculated for: $C_{14}H_{15}NO \cdot HCl$: 67.33% C; 6.46% H; 5.61% N. Found: 67.45% C; 6.42% H; 5.49%

N.

d. A solution of 1.8 g. of cyclopropylcarbonyl chloride in 50 ml. of dry chloroform is added dropwise to a cooled mixture of 3.1 g. of 2-phenyl-4,6,7,8-tetrahydrofuro[3,2-c]azepine and 1.7 g. of triethylamine in 50 ml. of dry chloroform. After addition, the reaction mixture is stirred at ambient temperature for 20 hours, washed with water and dried. The chloroform is removed and the residue is triturated with n-hexane to produce a solid product. The product is recrystallized from n-hexane to give 2-phenyl-5-cyclopropylcarbonyl-4,6,7,8-tetrahydrofuro[3,2-c]azepine, m.p. 108°–110°C.

Analysis: Calculated for $C_{18}H_{19}NO_2$: 76.84% C; 6.81% H; 4.98% N. Found: 76.83% C; 6.82% H; 5.10% N.

EXAMPLE 2

A solution of 8.2 g. of 2-phenyl-5-cyclopropylcarbonyl-4,6,7,8-tetrahydrofuro[3,2-c]azepine in 60 ml. of dry tetrahydrofuran is added to a refluxing solution of 2.3 g. of lithium aluminum hydride in 200 ml. of dry tetrahydrofuran. The reaction mixture is allowed to reflux for 20 hours, cooled and quenched with water and then with a saturated ammonium chloride solution. The mixture is filtered and the organic layer is collected, washed with water and dried. The solvent is removed, leaving a yellow oil. The hydrochloride salt is prepared, and the salt is recrystallized from an isopropanol-ether mixture to give 2-phenyl-5-cyclopropylmethyl-4,6,7,8-tetrahydrofuro[3,2-c]azepine hydrochloride, m.p. 245°C., dec.

Analysis: Calculated for $C_{18}H_{21}NO \cdot HCl$: 71.15% C; 7.30% H; 4.61% N. Found: 70.87% C; 7.40% H; 4.50% N.

EXAMPLES 3–6

By following the manipulative procedure described in Example 1d and substituting for cyclopropylcarbonyl chloride the appropriate carbonyl compounds indicated in Table I, 2-phenyl-4,6,7,8-tetrahydrofuro[3,2-c]azepines that are correspondingly substituted in the 5-position are obtained.

Table I

| Ex. | Carbonyl Compound | Recryst'n Solvent | m.p.°C. | Empirical Formula | % C | Calc. % H | % N | Found % C | % H | % N |
|---|---|---|---|---|---|---|---|---|---|---|
| 3 | acetyl chloride | n-hexane | 65–66 | $C_{16}H_{17}NO_2$ | 75.27 | 6.71 | 5.49 | 75.03 | 6.65 | 5.47 |
| 4 | chloroacetyl chloride | n-hexane/ ethylacetate | 95–97 | $C_{16}H_{16}ClNO_2$ | 66.32 | 5.57 | 4.84 | 65.85 | 5.58 | 4.69 |
| 5 | ethylchloroformate | n-hexane | 70–71 | $C_{17}H_{19}NO_3$ | 71.56 | 6.71 | 4.91 | 71.62 | 6.69 | 4.77 |
| 6 | 3,4,5-trimethoxybenzoyl chloride | n-hexane/ ethylacetate | 130–131 | $C_{24}H_{25}NO_5$ ½ $H_2O$ | 68.88 | 6.26 | 3.35 | 69.15 | 6.29 | 2.97 |

EXAMPLES 7–9

By following the manipulative procedure described in Example 2, reduction of the compounds of Examples 3, 5 and 6 produces the corresponding azepines of the invention as indicated in Examples 7, 8 and 9, respectively, of Table II.

Table II

| Ex. | Substituent in 5-position | Recryst'n Solvent | Empirical Formula | % C | Calc'd % H | % N | Found % C | % H | % N |
|---|---|---|---|---|---|---|---|---|---|
| 7 | $C_2H_5-$ | isopropanol-ether | $C_{16}H_{19}NO$ HCl | 69.17 | 7.26 | 5.04 | 68.76 | 7.27 | 4.97 |
| 8 | $CH_3-$ | isopropanol-ether | $C_{15}H_{17}NO$ HCl | 68.30 | 6.88 | 5.31 | 68.21 | 7.12 | 5.21 |
| 9 | $(CH_3O)_3PhCH_2-$ | ethylacetate | $C_{24}H_{27}NO_4$ HCl $H_2O$ | 64.35 | 6.75 | 3.13 | 64.01 | 6.61 | 3.31 |

EXAMPLE 10

A mixture of 7.9 g. of 2-phenyl-4,6,7,8-tetrahydrofuro[-[3,2-c]azepine (Example 1c), 100 ml. of n-butanol, 9.8 g. of γ-chloro-p-fluorobutyrophenone ethylene glycol ketal, 20.0 g. of potassium carbonate, and a few crystals of potassium iodide is allowed to reflux for 3 days at 120°C., and then filtered. The filtrate is concentrated to a dark residue. The residue is stirred for one hour with 100 ml. of ethanol and 100 ml. of 3N hydrochloric acid, the pH is adjusted to 10 with sodium hydroxide, and the mixture is extracted with benzene. The benzene extracts are washed with water, dried and concentrated to a dark oil. The oil is converted to the hydrochloride salt which is recrystallized from an ethyl acetate-methanol mixture to give crystals, m.p. 193°–195°C. dec., of 2-phenyl-5-[3-(p-fluorobenzoyl)-propyl]-4,6,7,8-tetrahydrofuro[3,2-c]-azepine hydrochloride.

Analysis: Calculated for: $C_{24}H_{24}FNO_2 \cdot HCl$: 69.64% C; 6.09% H; 3.38% N. Found: 69.31% C; 6.10% H; 3.30% N.

EXAMPLE 11

A mixture of 6.0 g. of 2-phenyl-5-chloroacetyl-4,6,7,8-tetrahydrofuro[3,2-c]azepine (Example 4), 3.8 g. of 4-(o-methoxyphenyl)piperazine, 2.0 g. of triethylamine and 60 ml. of dry methanol is stirred at ambient temperature for 24 hours and then at 50°C. for 4 hours. The solvent is removed, leaving a brown residue which is dissolved in chloroform. The chloroform solution is washed with water, dried, and concentrated to a brown oil which is triturated with n-hexane to produce a solid. This solid is recrystallized from an n-hexane-ether mixture to give crystals, m.p. 55°C., of 2-phenyl-5-[4-(o-methoxyphenyl)piperazinyl]-acetyl-4,6,7,8-tetrahydrofuro[3,2-c]azepine.

Analysis: Calculated for: $C_{27}H_{31}N_3O_3.H_2O$: 69.95% C; 7.17% H; 9.06% N. Found: 69.92% C; 6.91% H; 8.80% N.

EXAMPLE 12 a. 6.0 g. of aniline are added to a stirred solution of 15 g. of 2-phenacyl-1,3-cyclohexanedione in 50 ml. of glacial acetic acid. The mixture is allowed to reflux under nitrogen for 24 hours and then poured into water to precipitate a tan solid. The solid is collected, washed with water, dried, and recrystallized from isopropanol to give crystals, m.p. 194°–196°C., of 1,2-diphenyl-4-oxo-4,5,6,7-tetrahydroindole.

b. 4.6 g. of sodium azide are added portionwise over a period of 30 minutes to a solution of 20 g. of 1,2-diphenyl-4-oxo-4,5,6,7-tetrahydroindole in 150 g. of polyphosphoric acid. The mixture is stirred under nitrogen for 24 hours at 60°C., then for 24 hours at 100°C., and then poured into water. The resulting tan precipitate is collected, washed with water, dried and recrystallized from methanol to give crystals, m.p. 280°C., of 1,2-diphenyl-4-oxo-1,4,5,6,7,8-hexahydropyrrolo[3,2-c]azepine.

c. A suspension of 5 g. of 1,2-diphenyl-4-oxo-1,4,5,6,7,8-hexahydropyrrolo[3,2-c]azepine in 100 ml. of dry tetrahydrofuran is added, under nitrogen, to a stirred suspension of 0.8 g. of lithium aluminum hydride in 50 ml. of dry tetrahydrofuran. The mixture is refluxed for 6 hours under nitrogen and allowed to stand overnight at ambient temperature. The reaction mixture is cooled and 50 ml. of ether, 50 ml. of ethyl acetate and 75 ml. of 2N hydrochloric acid are added. The aqueous portion is collected, and the organic portion is extracted with 2N hydrochloric acid. The aqueous acidic layers are combined, adjusted to a pH of 10 with sodium carbonate solution, and extracted with ether. The ether extracts are washed with water and dried. The ether solution is filtered and the solvent is removed to give a solid. The product is recrystallized from n-hexane to give crystals, m.p. 157°–160°C., of 1,2-diphenyl-1,4,5,6,7,8-hexahydropyrrolo[3,2-c]azepine.

Analysis: Calculated for: $C_{20}H_{20}N_2$: 83.29% C; 6.99% H; 9.72% N. Found: 83.20% C; 7.17% H; 9.57% N.

d. By following the manipulative procedure described above in Example 1d, 9.0 g. of 1,2-diphenyl-1,4,5,6,7,8-hexahydropyrrolo[3,2-c]azepine, 3.1 g. of acetyl chloride and 4.1 g. of triethylamine produce 1,2-diphenyl-5-acetyl-1,4,5,6,7,8-hexahydropyrrolo[3,2-c]azepine. This compound is recrystallized from a hexane-ethyl acetate mixture to give a solid, m.p. 174°–176°C.

Analysis: Calculated for: $C_{22}H_{22}N_2O$: 79.96% C; 6.71% H; 8.48% N. Found: 79.85% C; 6.71% H; 8.31% N.

EXAMPLE 13

By following the manipulative procedure described in Example 2, 1,2-diphenyl-5-acetyl-1,4,5,6,7,8-hexahydropyrrolo[3,2-c]azepine (Example 12), is reduced to 1,2-diphenyl-5-ethyl-1,4,5,6,7,8-hexahydropyrrolo[3,2-c]azepine hydrochloride, m.p. 238°C.

Analysis: Calculated for: $C_{22}H_{24}N_2.HCl$: 74.87% C; 7.14% H; 7.94% N. Found: 74.75% C; 7.12% H; 7.88% N.

EXAMPLE 14

A mixture of 3.5 g. of 1,2-diphenyl-1,4,5,6,7,8-hexahydropyrrolo[3,2-c]azepine (Example 12c), 4.2 g. of 1-chloro-4,4-bis-(p-fluorophenyl)-butane, 5.3 g. of sodium carbonate, a few crystals of potassium iodide, and 100 ml. of 4-methyl-2-pentanone is allowed to reflux for 5 days at 120°C., then cooled and filtered. The filtrate is concentrated to a dark semisolid which is treated with etheral hydrogen chloride to provide a solid. The solid is recrystallized from benzene to give crystals, m.p. 107°C. dec., of 1,2-diphenyl-5-[4,4-bis-(p-fluorophenyl)-butyl]-1,4,5,6,7,8-hexahydropyrrolo[3,2-c]azepine hydrochloride.

Analysis: Calculated for: $C_{36}H_{34}F_2N_2.HCl.H_2O$: 73.63% C; 6.35% H; 4.77% N. Found: 73.03% C; 6.36% H; 4.82% N.

EXAMPLE 15

A mixture of 5.0 g. of 1,2-diphenyl-1,4,5,6,7,8-hexahydropyrrolo[3,2-c]azepine (Example 12c), 3.4 g. of isopropyl iodide, 20 g. of anhydrous potassium carbonate, a few crystals of potassium iodide and 100 ml. n-butanol is allowed to reflux for 72 hours at 120°C. The mixture is filtered and the filtrate is evaporated to a dark residue which is dissolved in chloroform. The chloroform solution is washed with water, dried and concentrated to a dark residue which is converted to a hydrochloride salt. The salt is recrystallized from an isopropanol-ether mixture to give crystals, m.p. 205°–208°C. dec., of 1,2diphenyl-5-isopropyl-1,4,5,6,7,8-hexahydropyrrolo[3,2-c]azepine hydrochloride.

Analysis: Calculated for: $C_{23}H_{26}N_2.HCl.H_2O$: 71.76% C; 7.59% H; 7.28% N. Found: 71.97% C; 7.59% H; 7.05% N.

EXAMPLE 16

A mixture of 4.5 g. of 1,2-diphenyl-1,4,5,6,7,8-hexahydropyrrolo[3,2-c]azepine (Example 12c), 2.8 g. of 1-bromo-3-methyl-2-butene, 20.0 g. of anhydrous potassium chloride, a few crystals of potassium iodide, and 100 ml. of n-butanol is allowed to reflux for 2 days at 120°C., poured into water and extracted with chloroform. The chloroform extracts are washed with water, dried and concentrated to a dark oil. The oil is converted to an oxalate salt which is recrystallized from an ethyl acetate-ether mixture to give crystals, m.p. 110°C., dec., of 1,2-diphenyl-5-(3-methyl-2-butenyl)-1,4,5,6,7,8-hexahydropyrrolo[3,2-c]azepine oxalate.

Analysis: Calculated for: $C_{25}H_{28}N_2.(CO_2H)_2$: 72.62% C; 6.77% H; 6.28% N. Found: 72.25% C; 6.65% H; 6.46% N.

EXAMPLE 17

A mixture of 4.5 g. of 1,2-diphenyl-1,4,5,6,7,8-hexahydropyrrolo[3,2-c]azepine (Example 12c), 4.4 g. of γ-chloro-p-fluoro-butyrophenone ethylene glycol ketal, 20.0 g. of anhydrous potassium carbonate, a few crystals of potassium iodide and 100 ml. of n-butanol is allowed to reflux for 72 hours at 120°C., filtered, and concentrated to a dark residue. The residue is stirred for one hour in a solution of 100 ml. of ethanol and 100 ml. of 3N hydrochloric acid, the pH is adjusted to 10 with sodium hydroxide, and the mixture is extracted with benzene. The benzene solution is washed with water, dried, and concentrated to a dark oil. The oil is converted to a hydrochloride salt which is recrystallized from an ethyl acetate-ether mixture to give crystals, m.p. 210°C., dec., of 1,2-diphenyl-5-[3-(p-fluorobenzoyl)propyl]-1,4,5,6,7,8-hexahydropyrrolo[3,2-c]azepine hydrochloride.

Analysis: Calculated for: $C_{30}H_{29}FN_2O.HCl.½H_2O$: 72.35% C; 6.27% H; 5.63% N. Found: 72.04% C; 6.07% H; 5.52% N.

EXAMPLE 18 a. 10 g. of cyclopropylamine are added dropwise to a mixture of 40.3 g. of 2-phenacyl-1,3-cyclohexanedione in 200 ml. of glacial acetic acid. The mixture is refluxed for 20 hours and poured into ice water. This mixture is stirred for 2 hours. A white solid, which precipitates, is collected and recrystallized from an isopropanol-ether mixture to give crystals, m.p. 170°–173°C., of 1-cyclopropyl-4-oxo-2-phenyl-4,5,6,7-tetrahydroindole.

b. To a cold solution of 10 g. of 1-cyclopropyl-4-oxo-2-phenyl-4,5,6,7-tetrahydroindole in 60 ml. of chloroform are added 20 ml. of concentrated sulfuric acid, and then 3.1 g. of sodium azide portionwise over a 60 minute span. The mixture is stirred at ambient temperature for 1 hour, and at 50°C. for 3 hours, allowed to stand at ambient temperature overnight, then poured over 500 g. of crushed ice, stirred for 1 hour, and extracted with chloroform. The chloroform solution is washed with water, dried and concentrated to a brown oil. Trituration with n-hexane yields a tan solid which is recrystallized from an isopropanol-ether mixture to give crystals, m.p. 215°C. dec., of 1-cyclopropyl-4-oxo-2-phenyl-1,4,5,6,7,8-hexahydropyrrolo[3,2-c]azepine.

c. A suspension of 5.0 g. of 1-cyclopropyl-4-oxo-2-phenyl-1,4,5,6,7,8-hexahydropyrrolo[3,2-c]azepine in 100 ml. of dry tetrahydrofuran is added to a refluxing stirred suspension of 1.5 g. of lithium aluminum hydride in 150 ml. of dry tetrahydrofuran under nitrogen. The mixture is refluxed for 20 hours, cooled in an ice-bath, quenched with 50 ml. of a saturated ammonium chloride solution and diluted with ether. The mixture is filtered and the organic layer is separated, washed with water and then dried. The solvent is removed, leaving a tan oil, which is triturated with petroleum ether to provide an off-white solid. Recrystallization from petroleum ether gives crystals, m.p. 116°–119°C., of 1-cyclopropyl-2-phenyl-1,4,5,6,7,8-hexahydropyrrolo[3,2-c]azepine.

d. A solution of 3.9 g. of acetyl chloride in 25 ml. of chloroform is added to a cooled solution of 11.0 g. of 1-cyclopropyl-2-phenyl-1,4,5,6,7,8-hexahydropyrrolo[3,2-c]azepine and 5.0 g. of triethylamine in 50 ml. of dry chloroform. The mixture is stirred at ambient temperature for 20 hours, washed with water, dried, and concentrated to provide 1-cyclopropyl-2-phenyl-5-acetyl-1,4,5,6,7,8-hexahydropyrrolo[3,2-c]azepine as an oil. The oil is treated according to the manipulative procedure described above in Example 2, to give crystals, m.p. 85°C. dec., of 1-cyclopropyl-2-phenyl-5-ethyl-1,4,5,6,7,8-hexahydropyrrolo[3,2-c]azepine oxalate.

Analysis: Calculated for: $C_{19}H_{24}N_2.(CO_2H)_2 .2H_2O$: 62.05% C; 7.44% H; 6.89% N. Found: 62.42% C; 6.89% H; 6.34% N.

EXAMPLE 19

A mixture of 3.5 g. of 1-cyclopropyl-2-phenyl-1,4,5,6,7,8-hexahydropyrrolo [3,2-c]azepine (Example 18c), 4.4 g. of γ-chloro-p-fluorobutyrophenone ethylene glycol ketal, 20.0 g. of anhydrous potassium carbonate, a few crystals of potassium iodide, and 100 ml. of n-butanol is treated according to the manipulative procedure described in Example 10, to give 1-cyclopropyl-2-phenyl-5-[3-(p-fluorobenzoyl)propyl]-1,4,5,6,7,8-hexahydropyrrolo[3,2-c]azepine hydrochloride, m.p. 130°C.

Analysis: Calculated for: $C_{27}H_{29}FN_2O.HCl.H_2O$: 68.85% C; 6.85% H; 5.95% N. Found: 68.85% C; 6.11% H; 6.03% N.

EXAMPLE 20 a. 6.6 g. of cyclopropylmethylamine are added dropwise to a solution of 21.5 g. of 2-phenacyl-1,3-cyclohexanedione in 100 ml. of glacial acetic acid. The mixture is refluxed for 20 hours. cooled, poured into ice water, stirred for 30 minutes, and extracted with chloroform. The chloroform solution is washed with water, dried, and concentrated to an oil. The oil is triturated with petroleum ether to provide a tan solid, which is recrystallized from n-hexane to give crystals, m.p. 101°–103°C., of 1-cyclopropylmethyl-4-oxo-2-phenyl-4,5,6,7-tetrahydroindole.

b. A sample of 1-cyclopropylmethyl-4-oxo-2-phenyl-4,5,6,7-tetrahydroindole is treated according to the manipulative procedure described in Example 18b to give 1-cyclopropylmethyl-4-oxo-2-phenyl-1,4,5,6,7,8-hexahydropyrrolo[3,2-c]azepine, m.p. 210°C., dec.

c. A suspension of 5.0 g. of 1-cyclopropylmethyl-4-oxo-2-phenyl-1,4,5,6,7,8-hexahydropyrrolo[3,2-c]azepine in 125 ml. of dry tetrahydrofuran is added to a refluxing solution of 1.3 g. of lithium aluminum hydride in 100 ml. of dry tetrahydrofuran. The mixture is allowed to reflux for 20 hours, cooled, quenched with 60 ml. of a saturated ammonium chloride solution, diluted with 100 ml. of ether and filtered.

The organic layer is collected, diluted with ether, washed with water, dried and concentrated to a brown oil. The oil is converted to a hydrochloride salt, which is recrystallized from an ethyl acetate-methanol mixture, to give crystals m.p. 190°C., dec., of 1-cyclopropylmethyl-2-phenyl-1,4,5,6,7,8-hexahydropyrrolo [3,2-c]azepine hydrochloride.

Analysis: Calculated for: $C_{18}H_{22}N_2 .HCl.½H_2O$: 69.32% C; 7.76% H; 8.99% N. Found: 69.57% C; 7.38% H; 8.88% N.

d. By following the manipulative procedure described in Example 18d, 1-cyclopropylmethyl-2-phenyl-1,4,5,6,7,8-hexahydropyrrolo[-[3,2-c]azepine is converted to 1-cyclopropylmethyl-2-phenyl-5-ethyl-1,4,5,6,7,8-hexahydropyrrolo[3,2-c]azepine hydrochloride, m.p. 180°C., dec.

EXAMPLE 21 a. 6.0 g. of n-propylamine are added dropwise to a solution of 24.0 g. of 2-phenacyl-1,3-cyclohexanedione in 100 ml. of glacial acetic acid. The mixture is refluxed for 20 hours, cooled, poured into ice water, stirred for 3 hours, and the resultant precipitate is collected, washed with water and dried. This solid is recrystallized from an isopropanol-ether mixture to give crystals, m.p. 89°–91°C., of 4-oxo-2-phenyl-1-propyl-4,5,6,7-tetrahydroinodole.

b. A sample of 4-oxo-2-phenyl-1-propyl-4,5,6,7-tetrahydroindole is treated according to the manipulative procedure described in Example 18b to give 4-oxo-2-phenyl-1-propyl-1,4,5,6,7,8-hexahydropyrrolo[3,2-c]azepine, m.p. 80°C., dec.

c. A solution of 3.5 g. of 4-oxo-2-phenyl-1-propyl-1,4,5,6,7,8-hexahydropyrrolo[3,2-c]azepine in 50 ml. of dry tetrahydrofuran is added to a refluxing solution of 1.0 g. of lithium aluminum hydride in 100 ml. of dry tetrahydrofuran. The mixture is allowed to reflux for 20 hours, cooled, quenched with 60 ml. of a saturated ammonium chloride solution, then diluted with 100 ml. ether, and filtered. The organic phase is separated, washed with water, dried, and concentrated to a brown oil, which is dissolved in ether, filtered, and converted to a hydrochloride salt. The salt is recrystallized from an isopropanol-ether mixture to give crystals, m.p. 110°C., of 1-propyl-2-phenyl-1,4,5,6,7,8-hexahydropyrrolo[3,2-c]azepine hydrochloride.

d. By following the manipulative procedure described in Example 18d, 1-propyl-2-phenyl-1,4,5,6,7,8-hexahydropyrrolo[3,2-c]azepine is converted to 1-propyl-2-phenyl-5-ethyl-1,4,5,6,7,8-hexahydropyrrolo[3,2-c]azepine hydrochloride hydrate, m.p. 120°C.

Analysis: Calculated for: $C_{19}H_{26}N_2 \cdot HCl \cdot H_2O$: 67.73% C; 8.68% H; 8.32% N. Found: 68.20% C; 8.26% H; 8.07% N.

We claim:

1. A compound of the formula

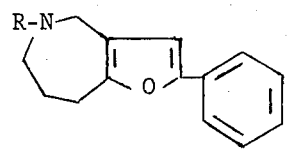

wherein R is alkanoyl of from 2 to 6 carbon atoms, haloalkanoyl of from 2 to 6 carbon atoms, alkoxycarbonyl of from 2 to 6 carbon atoms, cycloalkylcarbonyl of from 4 to 7 carbon atoms, benzoyl, alkoxybenzoyl of from 8 to 10 carbon atoms, halobenzoyl or halobenzoylalkyl of from 8 to 11 carbon atoms, and a physiologically tolerable acid addition salt thereof.

2. A compound as defined in claim 1 in which R is acetyl, propionyl, butyryl, chloroacetyl, butoxycarbonyl, cyclopropylcarbonyl, cyclohexylcarbonyl, benzoyl, trimethoxybenzoyl, chlorobenzoyl or fluorobenzoylalkyl.

3. The compound defined in claim 2 which is 2-phenyl-5-acetyl-4,6,7,8-tetrahydrofuro[3,2-c]azepine.

4. The compound defined in claim 2 which is 2-phenyl-5-[3-(p-fluorobenzoyl)propyl]-4,6,7,8-tetrahydrofuro[3,2-c]azepine; and a physiologically tolerable acid addition salt thereof.

* * * * *